(12) United States Patent
Eyal et al.

(10) Patent No.: US 8,268,595 B2
(45) Date of Patent: Sep. 18, 2012

(54) INTEGRATED METHODS FOR PROCESSING PALM FRUIT BUNCHES

(75) Inventors: Aharon Eyal, Jerusalem (IL); Carmi Raz, Gizo (IL)

(73) Assignee: Eyal Researach Consultants Ltd. (IL)

(*) Notice: Subject to any disclaimer, the term of this patent is extended or adjusted under 35 U.S.C. 154(b) by 443 days.

(21) Appl. No.: 12/648,483

(22) Filed: Dec. 29, 2009

(65) Prior Publication Data

US 2010/0167351 A1    Jul. 1, 2010

Related U.S. Application Data

(60) Provisional application No. 61/141,091, filed on Dec. 29, 2008.

(51) Int. Cl.
| | |
|---|---|
| *C12P 19/00* | (2006.01) |
| *C12P 17/06* | (2006.01) |
| *C12P 5/00* | (2006.01) |
| *C12P 7/02* | (2006.01) |
| *C12P 7/08* | (2006.01) |
| *C12P 7/16* | (2006.01) |
| *C12P 7/28* | (2006.01) |
| *C12P 7/62* | (2006.01) |
| *C12N 9/00* | (2006.01) |

(52) U.S. Cl. .......... 435/72; 435/125; 435/134; 435/135; 435/150; 435/155; 435/160; 435/163; 435/166; 435/183

(58) Field of Classification Search ............ 435/72, 435/125, 134, 135, 150, 155, 160, 163, 166, 435/183

See application file for complete search history.

(56) References Cited

U.S. PATENT DOCUMENTS

| | | | | |
|---|---|---|---|---|
| 5,650,555 | A * | 7/1997 | Somerville et al. | 800/264 |
| 5,792,931 | A * | 8/1998 | Duvick et al. | 800/301 |
| 6,025,188 | A * | 2/2000 | Duvick et al. | 435/267 |
| 6,942,994 | B2 * | 9/2005 | Nikolau et al. | 435/69.2 |
| 2009/0203094 | A1 * | 8/2009 | Cirpus et al. | 435/134 |
| 2011/0020874 | A1 * | 1/2011 | Hata | 435/72 |

* cited by examiner

*Primary Examiner* — Herbert J Lilling

(74) *Attorney, Agent, or Firm* — Kilpatrick Townsend & Stockton LLP

(57) ABSTRACT

This invention is directed to an integrated method for the processing of palm fruit bunches to oil and other products. The method comprises inter alia separating palm fruit carrying bunches into fruits and lignocellulosic empty fruit bunches, processing the fruits to form palm oil, and at least one lignocellulosic processing coproduct; generating an aqueous stream; producing a non-oil, non-alcohol, non-fatty acid ester third product from the oil, the lignocellulosic processing coproduct, the aqueous stream or from a combination thereof; processing at least a portion of the lignocellulosic empty fruit bunches, lignocellulosic processing coproduct or a combination thereof into a fourth product and optionally producing at least one fifth conversion product from the fourth product; and using at least a portion of the fourth product or a product of its conversion or a combination thereof.

40 Claims, No Drawings

INTEGRATED METHODS FOR PROCESSING PALM FRUIT BUNCHES

RELATED APPLICATION

This application claims priority to U.S. Application No. 61/141,091, filed Dec. 29, 2008, the disclosure of which is incorporated by reference in its entirety for all purposes.

FIELD OF THE INVENTION

The present invention relates to integrated methods for processing palm fruit bunches.

BACKGROUND

Large amounts of palm oil are produced every year in oil palm growing countries, such as Malaysia and Indonesia. Palm fresh fruit bunches (FFB) are processed in palm oil mills to palm oil, multiple lignocellulosic coproducts and an aqueous effluent referred to as palm oil mill effluent (POME). About 2.5 tons of POME are produced per ton of oil. Part of the lignocellulosic material is burned for process energy, but most of it is not usefully applied. In some cases electricity is produced during this process, however, some of the lignocellulosic material is not used due to difficulties in burning it.

POME presents a major problematic environmental issue. It is hot (80-90° C.) and slightly acidic. Reported concentration ranges for oil/grease levels, BOD (biological oxygen demand), COD (chemical oxygen demand) and solids (suspended+dissolved) in POME are 4-17 g/L, 10-44 g/L, 20-100 g/L and 10-80 g/L respectively. On an elemental basis, of particular importance are carbon (about 25 g/L), potassium (2.3 g/L), nitrogen (0.8-1.4 g/L) and phosphorous (0.8 g/L). Several transition metals, such as iron, manganese, copper and zinc are found in POME at milligrams/L levels.

POME represents major oil yield losses. Oil droplets in POME consist of more than 80% neutral lipids, out of which >80% are triglycerides and most of the rest are diglycerides and 8.0% free fatty acids.

Due to its high BOD content, POME cannot be discharged to the environment as such and is biologically treated. Typically, processing of POME consists of employing a train of anaerobic, aerobic and/or facultative (anaerobic and aerobic) processes. The end products of anaerobic processing are mainly biogas (a mixture of methane 60-70% and $CO_2$, 30-40%) and bio-solids and the end products of aerobic processing are essentially $CO_2$ and bio-solids. The three most common treatment systems used are ponding systems, open tank digesters with extended aeration and closed tank digesters with biogas recovery and land applications. Hydraulic retention times in anaerobic and facultative ponding systems in open tank digesters or closed tank digesters are in the range of 20-45 and 16-20 days, respectively, which requires the use of large treatment systems, whose operation presents major difficulties. For example, in ponding systems, mixing is achieved by biogas bubbling which is inadequate for complete mixing, and leads to development of dead spots and short-circuiting in the ponds and therefore low efficiency. Oil delivered to anaerobic ponds tends to agglomerate and the rising solids brought to the surface by the biogas forms a sticky scum that is difficult to remove. Solids tend to build up in the ponds and regular de-sludging of the ponds is required. There is an urgent need to improve such systems and to minimize the environmental problems associated therewith.

The lignocellulosic coproducts of palm oil production are rich in polysaccharides (mainly cellulose and hemi-cellulose). Hydrolyzing such polysaccharides generates fermentable sugars. Many chemical and biological methods have been developed for the hydrolysis of the polysaccharides and subsequent fermentation of such fermentable sugars to form various fermentation products, mainly ethanol. Methods for the conversion of lignocellulosic material to fermentables other than sugars are known, as well.

Gutiérrez et. al. ("Process integration possibilities for biodiesel production from palm oil using ethanol obtained from lignocellulosic residues of oil palm industry" Bioresource Technology 100 (2009) 1227-1237) describe a process, whereby palm oil is produced from Fresh Fruit Bunches by commercial methods, sugars from lignocellulosic coproducts are fermented to ethanol, which is concentrated by distillation and dried on molecular sieves and then reacted with the palm oil in an extractive trans-esterification process to form ethyl esters of fatty acids, referred to as biodiesel, and glycerol. The following integration options were described in Gutiérrez:

- Simultaneous saccharification and co-fermentation (SSCF): formation of hexoses and pentoses and simultaneous fermentation of the same
- Consolidated bioprocessing (CBP): one microbial community is employed both for the production of cellulose hydrolytic enzymes and fermentation.
- Reaction-separation integration in the multi-stage reactor-extractor for the trans-esterification.
- Recirculation of material streams in order to achieve a better utilization of sugars, e.g. by implementing the recycling of water streams. The bottoms of ethanol rectification column and a fraction of the thin stillage are recycled back to the washing step of lignocellulosic biomass leaving the dilute acid pretreatment reactor. Thus, non-consumed pentoses and hexoses return to the SSCF reactor to be converted into ethanol.
- The secondary steam from evaporators is condensed and recycled back to the pretreatment reactor where it is used as process water.
- Recirculation of the distillate from the distillation column used for glycerol separation. This stream is fed to the rectification column in the ethanol production line.
- The rectification column is also fed with the regenerate resulting from the adsorption in the molecular sieves.
- Energy integration between both production lines: The heat released during the condensation of overhead vapors exiting the concentration and rectification columns is employed to provide the energy required by the flash unit processing the glycerol-enriched stream that leaves the reactor-extractor.
- The purification of the two streams exiting the multi-stage reactor-extractor undergoes distillation using two columns and forming two ethanol-enriched streams. Those streams are recycled back to the reactor-extractor.
- Energy integration by using the available heat of the condensers of both concentration and rectification columns in the ethanol production line for the distillation column employed for glycerol purification.

While the integration processes suggested by Gutiérrez et. al., save on energy costs, they do not address some of the major problems of the palm oil industry, including yield losses, major environmental issues and poor economics. Gutiérrez et. al also produce a limited repertoire of products from the integrated processes he describes.

SUMMARY OF THE INVENTION

With this state of the art in mind, there is now provided according to the present invention an integrated method for the processing of palm fruit bunches to oil and other products, said method comprising:

a. providing palm fruit carrying bunches and separating said palm fruit carrying bunches into fruits and lignocellulosic empty fruit bunches;

b. processing said fruits to form palm oil, and at least one lignocellulosic processing coproduct;

c. generating an aqueous stream while carrying out step (a), step (b) or both;

d. producing a non-oil, non-alcohol, non-ester third product from said oil, said lignocellulosic processing coproduct, said aqueous stream or from a combination thereof;

e. processing at least a portion of said lignocellulosic empty fruit bunches, lignocellulosic processing coproduct or a combination thereof into a fourth product and optionally producing at least one fifth conversion product from said fourth product; and f. using at least a portion of said fourth product or a product of its conversion or a combination thereof in said processing in step (b), said producing in step (d), or in a combination thereof.

In one embodiment, the fourth product is a fermentable compound, and said method comprises fermenting said fermentable compound into at least one fermentation product, which fermentation product which in some embodiments, will be referred to hereinafter as the fifth conversion product, it being understood that other fermentation products, which are not conversion products are also to be considered as part of this invention. According to this aspect, and in one embodiment, the fermentation product is selected from the group consisting of alcohols, hydrocarbons and esters. In another embodiment, the fermentation product is an ester and said ester is selected from the group consisting of esters of fatty acids. In another embodiment, the fermentation product is an alcohol formed in a fermentation liquor, and the method further comprises the step of concentrating said alcohol in a distillation column. In yet another embodiment, the fermentation product is an alcohol, and the method further comprises the step of reacting the palm oil, palm oil fatty acids or both with the alcohol and producing a fatty acid ester of the alcohol. In another embodiment, the fermentation product is an alcohol selected from the group consisting of ethanol, propanols, butanols and pentanols or a combination thereof. In yet another embodiment, the fatty acid is reacted with said fermentation product and in another embodiment, at least one fatty compound is extracted by means of said fermentation product, wherein said fatty compound is selected from a group consisting of fatty acids, oil and low-grade oil, further comprising the step of reacting said fatty compound with an alcohol to form their ester. In one embodiment, the fermentation product is an alcohol and the fatty acids are reacted with the alcohol. In yet another embodiment, the converting comprises hydrolysis, thermal treatment or a combination thereof and in one embodiment, hydrolysis comprises treatment with sulfuric acid, hydrochloric acid, another acid, enzymes with cellulose hydrolyzing capacity, enzymes with hemi-cellulose hydrolyzing capacity, and combinations thereof. In some embodiments, a wet matter is formed and the fermentation product is ethanol, and the method further comprises a step of drying said wet matter by contacting the wet matter with ethanol to form dried matter and diluted ethanol. In some embodiments, the method further comprises the steps of producing a biodiesel by producing an ester and mixing the fermentation product with the ester.

In another embodiment, at least one of said third product, said fourth product and said fifth product is selected from a group consisting of a vitamin, a flavonoid, a phenolic acid, a hydroxy acid, a sugar, a fertilizer, a polymerizable compound, acetone, an enzyme, a carotenoid and their combinations.

In another embodiment, the method further comprises treating said palm fruit carrying bunches with steam, water or a combination thereof at elevated temperatures and generating said aqueous stream.

In another embodiment, processing said fruits comprises digestion, pressing to form crude oil and press cake, separation of fine solids from the crude oil, clarification of said crude oil forming clarified oil and an aqueous effluent, dehydration of clarified oil to form dehydrated clarified oil, treating said press cake for separation of nuts from palm press fiber, cracking said nuts to separate kernels from the palm kernel shell, milling said kernels for extracting palm kernel oil and separating said palm kernel oil from palm kernel cake or combinations thereof.

According to this aspect, and in some embodiments, processing further comprises refining said clarified oil, dehydrated clarified oil, palm kernel oil and mixtures thereof or combinations thereof and wherein refining comprises degumming, deacidufication or combinations thereof, and producing a refined oil and at least one of a gum, fatty acid and fatty acid alkali salt.

According to this aspect, and in some embodiments, the processing generates an aqueous stream, which comprises an aqueous effluent. In some embodiments, the fourth product is a fermentable compound, and the method comprises fermenting said fermentable compound into a fermentation product. According to this aspect, and in one embodiment, the method further comprises the step of treating at least one of the gums, fatty acids and fatty acid alkali salt with the fermentation product and in another embodiment, the method further comprises the step of fractionating said oil by means of extraction with said fermentation product.

In some embodiments, the lignocellulosic processing coproduct comprises a palm press fiber, a palm kernel shell, a palm kernel cake or combinations thereof. In some embodiments, processing said fruit comprises oil extraction from digested fruit, press cake, separated fine solids, aqueous effluent or products of its treatment, kernel cake or combinations thereof. According to this aspect and in some embodiments, the method comprises converting said lignocellulosic empty fruit bunches, lignocellulosic processing coproduct or a combination thereof into a fermentable product and said method comprises fermenting said fermentable product into a fermentation product. According to this aspect and in some embodiments, the oil extraction is by means of said fermentation product, products thereof and their combinations. In some embodiments, the oil extraction utilizes a concentrated solution of a fermentation product selected from the group of alcohols, and said method further comprises the step of forming an extract comprising said oil and said alcohol.

According to this aspect and in some embodiments, the oil is recovered from said extract by adding water to said extract, whereby an oil phase and a diluted alcohol phase are formed and in some embodiments, the extract is used for the production of a fatty acid ester.

In another embodiment of the invention, the fourth or fifth product is an ester, which in some embodiments is an ester of a fatty acid.

In another embodiment of the invention, producing at least one of said third product, said fourth product and said fifth product comprises extraction of said third or fourth product from said aqueous stream or from an aqueous fermentation liquor. According to this aspect and in one embodiment, the third product is a fermentable product and said method comprises fermenting said fermentable product into a fermentation product. Also according to this aspect and in one embodiment, the extraction is by means of said fermentation product, products thereof and their combinations and in some embodiments, the method further comprises the step of concentrating or separating insoluble materials in said aqueous stream prior to extraction. Also according to this aspect and in one embodiment, the method further comprises the step of concentrating said aqueous solution, separating insoluble materials in said aqueous stream or both, prior to extraction.

In another embodiment of the invention, the third product is a biological compound. According to this aspect of the invention and in one embodiment, the fourth product is a fermentable compound, and said method comprises fermenting said fermentable compound into a fermentation product. Also according to this aspect and in another embodiment, the biological product is separated utilizing said fermentation product. In one embodiment, the biological compound is formed by biological conversion and in one embodiment, the biological conversion is selected from a group consisting of (i) growing algae in said generated aqueous stream, (ii) fermenting carbon sources in said aqueous stream and (iii) fermenting said fermentables and combinations thereof.

DETAILED DESCRIPTION OF THE INVENTION

This invention provides integrated methods for the processing of palm carrying fruit bunches to palm oil and other products. While processes for the production of palm oil are known, the methods utilized to date suffer numerous limitations including significant amounts of POME production, without effective means for utilization of the POME. POME, in addition to representing a significant oil yield loss, poses a severe environmental problem.

The present invention provides methods for processing palm fruit carrying bunches to palm oil that overcome the above-recited limitation. The methods provide for the generation of multiple useful byproducts of the processing of the palm fruit carrying bunches to palm oil, and the integration of some of such products to arrive at other useful products, increasing the efficiency of such methods, while diminishing the negative environmental impact of what previously had been high amounts of waste products. Moreover, the byproducts are in turn applied to the generation of greater yields of palm oil, as well as the enhanced generation of useful by-products, such that the integrated methods of this invention represent a marked improvement in the efficiency of processes for the production of palm oil while concurrently diminishing the negative environmental impact of such processes. In some embodiments, the processes are conducted at the same plant or facility or in proximity to each other.

In one embodiment, the integrated methods of the invention comprise separating said palm fruit carrying bunches into fruits and lignocellulosic empty fruit bunches. Such separation may be conducted via any means known in the art. In one embodiment, the separation includes exposing the fruit carrying bunches to saturated steam, which favors the removal of fruits from the oil, and fruit removal may then be carried out via multiple means, such as, for example, via the aid of a rotary drum thresher. Empty fruit bunches (EFB) and an aqueous effluent (which may also be referred to as "sterilizer condensate") may be formed along with the separated fruits. The aqueous effluent is high in BOD, oil, grease, suspended solids and dissolved solids.

The methods of this invention provide for further processing of such separated fruits to form palm oil, and at least one lignocellulosic processing coproduct.

The terms "at least one", as well as the terms "a" or "an" with regard to the indicated material when utilized herein, refer to the inclusion of one or more of such material. It is to be understood that the term "at least one of a group of" when referring to generic groups refers to inclusion of one species of each generic group described, as well as multiple species within each group. Similarly, the term "or combinations thereof" when describing combinations of generic groups is to be understood to refer to one of each generic group, or combinations of multiple species from the indicated genera, in any combination, including multiple species of a single genus, multiple species of only some of the listed genera or one or more species of every genus listed.

Processing of the fruits to form palm oil may be via any known means, for example, by digestion in cylindrical vertical tanks with stirring at 100° C. In some embodiments, the mashing is followed by separation of the pulp from the nuts and subsequent processing of the mashed fruits in a screw press where crude oil is then separated from the resulting cake. In some embodiments, an aqueous stream is generated during the processing of the fruits to oil. In some embodiments, fresh fruit bunches are exposed to steam and/or water at elevated temperatures thereby generating an aqueous stream.

In some embodiments, the aqueous effluent generated as described is formed at a rate of about 1 ton effluent per ton of oil produced.

In some embodiments, the oil is passed through vibrating screens for removal of any fine solids, following which the oil is clarified in decanters. In some embodiments, the clarified oil contains about 1% water and is therefore subsequently dehydrated, prior to use/storage. In some embodiments, hot water (about 90° C.) is added to the oil to accelerate the process and decanter cake is obtained.

In some embodiments, sludge from the decanter (also referred to as separator sludge) is subjected to centrifugation and oil is recovered.

The process further entails processing the press cake or decanter cake to separate the palm press fibers (PPF) from the palm nuts. Nuts may be further processed to separate kernels from palm kernel shell (PKS), and kernels may be further processed to extract palm kernel oil (PKO) and palm kernel cake (PKC). Lignocellulosing processing coproducts comprise PPF, PKS and PKC, and the separated fruits are processed to form palm oil, and at least one lignocellulosic processing coproduct. As used here, the term palm oil refers to the oil separated in the screw press, to palm kernel oil, to such oils after various refining steps and combinations thereof. In some embodiments, PPF is a specific lignocellulosic processing coproduct produced in the processes of this invention, as is EFB.

In some embodiments, the fruit is processed by any number of means, including, for example, digestion of the fruit such as mashing, pressing of the fruit to form crude oil and press cake, separation of fine solids from the crude oil, clarification of said crude oil forming clarified oil and an aqueous effluent, dehydration of clarified oil to form dehydrated clarified oil, treating the press cake for separation of nuts from palm press fiber, cracking said nuts to separate kernels from the palm kernel shell, milling said kernels for extracting palm kernel oil and separating said palm kernel oil from palm kernel cake as described hereinabove.

In some embodiments, the processing further comprises refining the clarified oil obtained, or in some embodiments, refining the dehydrated clarified oil, or in some embodiments, refining the palm kernel oil or in some embodiments, refining all of the above. In some embodiments, the term "refining"

refers to de-gumming or de-acidification, or their combination and in some embodiments, refining results in producing a refined oil and at least one additional product selected from gums, fatty acids and fatty acid alkali salts.

In some embodiments, crude oil contains triglycerides, phospholipids, free fatty acids (FFAs) and possibly several other components, some of which are of high nutritive or other value, e.g. carotenoids, while others are toxic.

In some embodiments, "refining" refers to de-gumming, de-acidification, bleaching or deodorization, and in some embodiments, "refining" refers to conducting any or all processes, which comprise refining the oil, as described herein. In some embodiments, the term "de-gumming" refers to contact with water whereby wetted phospholipids are formed and separated from the oil via centrifugation forming de-gummed oil and gums (a crude form of phospholipids). In one embodiment, alkali refining comprises de-acidification involving contact with an aqueous solution of an alkali, whereby FFAs are converted to their salt form (typically sodium salt, i.e. soap), which is removed by centrifugation to form de-acidified oil and soapstock. In some embodiments, degumming and alkali refining are combined into a single operation. In some embodiments, de-acidification is conducted by physical refining where FFAs are distilled for example by steam stripping degummed oil.

In some embodiments, the method further comprises the step of treating said at least one of said gums, fatty acids and fatty acid alkali salt with said fermentation product.

According to an embodiment, the method of the present invention further comprises the step of producing phospholipids, which producing comprises contacting gums generated on degumming of crude palm oil with said fermentation product. Gums separated on degumming (crude gums) contain phospholipids, water, oil and possibly some other components. Contacting with a fermentation product, e.g. ethanol separates oil and/or water from the phospholipids.

Alkali deacidification (removal of FFAs) forms salts of FFAs (e.g. sodium salts, i.e. soap), which are separated from the crude oil, e.g. by centrifugation. Acidulation with a strong acid forms salts of said acid and FFAs, which are separated to form FFAs-containing phase. That phase is further purified, according to a preferred embodiment, by contacting with a fermentation product, e.g. ethanol.

In some embodiments, the methods of this invention further comprise the step of fractionating the oil obtained by means of extraction with said fermentation product.

In some embodiments, such methods may be conducted by any known means, including known commercial practice, whereby palm oil is fractionated to at least two fractions differing in the degree of unsaturation of the fatty acids in the triglycerides. This degree of unsaturation indicates the number of double bonds on such fatty acids and may be measured by its iodine value (IV)—the amount of iodine, in grams, that is taken up by 100 grams of the oil, fat, or wax. Fully saturated oils take up no iodine; therefore their iodine value is zero; but unsaturated oils take up iodine. (Unsaturated compounds contain molecules with double or triple bonds, which are very reactive toward iodine.) The more iodine is attached, the higher is the iodine value, and the more reactive, less stable, softer, and more susceptible to oxidation and rancidification is the oil. Thus according to some practice, refined, bleached and deodorized palm oil with IV of 50-55 is commonly fractionated into an 56 IV olein and 48 IV stearine. According to a preferred embodiment of the present invention, such fractionation is conducted on contact with a fermentation product.

According to many of the embodiments of the present invention, the amount of energy available from lignin is sufficient for the needs of the production of palm oil, fermentables, fermentation products and said third product.

The term "bleaching" as used herein, refers in some embodiments, to the removal of color from the oil, while the term "deodorization" as used herein, refers in some embodiments, to distillation of undesired compounds, e.g. ones that contribute undesired odor and/or are toxic. In some embodiments, refined, bleached and deodorized palm oil having an Iodine Value (IV) of 50-55 is commonly fractionated into a 56 IV olein and 48 IV stearine (IV is a common measure of the degree of unsaturation of the fatty acids in the oil).

In some embodiments, the processing step in the methods of this invention comprises clarification as described herein, and the aqueous stream generated during the processing comprises the aqueous effluent.

In some embodiments, the aqueous stream formed during oil separation from the prior aqueous stream (also referred to as separator sludge) is formed at a rate of about 1.5 tons per ton of oil and is high in BOD, oil+grease, suspended solids and dissolved solids.

The term "about" as used herein, when in reference to a numerical value or range is to be understood as encompassing a value representing a variance of at least ±1% about said value. In some embodiments, the term "about" encompasses a value representing a variance of at least ±2% about said value, or in some embodiments, ±2.5% about said value, or in some embodiments, ±3% about said value, or in some embodiments, ±4% about said value, or in some embodiments, ±5% about said value, or in some embodiments, ±7.5% about said value, or in some embodiments, ±10% about said value.

In some embodiments, both sterilizer condensate and separator sludge are formed, and are combined into a single aqueous effluent stream, which is generated at a rate of about 2.5 tons/ton of oil and may be referred to as palm oil mill effluent (POME). In some embodiments, the POME generated during the processing steps of this invention is quite hot (80-90° C.) and slightly acidic, and may comprise reported concentration ranges for oil/grease levels, BOD (biological oxygen demand), COD (chemical oxygen demand) and solids (suspended+dissolved) of 4-17 g/L, 10-44 g/L, 20-100 g/L and 10-80 g/L respectively.

Known methods for processing fresh fruit bunches to form palm oil result in large quantity production of POME, therefore, in marked contrast to preferred embodiments of the subject Application. POME production represents major oil yield losses, as noted, and oil droplets in POME consist of more than 80% neutral lipids, out of which more than 80% are triglycerides with the remainder being diglycerides and about 8.0% free fatty acids. POME also contains glycolipids such as digalactosyl diglycerides (22%), steryl glycosides (17%), cerebroside (9%), monogalactosyl diglycerides (20%), and esterified steryl glycoside (26%); and phospholipids such as: phosphatidylethanolamine (21%), phosphatidylglycerol (37%), phosphatidylcholine (17%), and phosphatidylserine together with phosphatidylinositol at 11%.

In some embodiments, the processing steps of the methods of this invention generate palm oil and at least one lignocellulosic processing coproduct. In some embodiments, such lignocellulosic processing coproducts may comprise a palm press fiber (PPF), a palm kernel shell (PKS), a palm kernel cake (PKC), or multiples of each, or combinations thereof.

In some embodiments, the methods of this invention provide for better utilization of byproducts of palm oil production, which to date are poorly utilized.

In some embodiments of the methods of the present invention, separating palm fruit carrying bunches into fruits and processing the fruits yields lignocellulosic empty fruit bunches (EFB), lignocellulosic processing coproduct (PPF, PKS, PKC), multiples of each and combinations thereof. In some embodiments, the lignocellulosic empty fruit bunches and lignocellulosic processing coproduct may be commonly referred to as lignocellulosic material. In some embodiments, lignocellulosic materials may be converted into fermentables, a term which refers to materials, which provide carbon sources to fermentation and may undergo fermentation. In some embodiments, products which result from the fermentation of "fermentables" are referred to herein as "fermentation products".

In one embodiment, at least one EFB, PPF or combinations thereof are converted into a fermentable.

EFB and PPF are high in cellulose (about 45% and 40%, respectively) and hemicellulose (35% and 25%, respectively), which are polysaccharides, which when hydrolyzed, form fermentable sugars. EFB and PPF also contain about 20% w/w lignin each and ashes. PPF is also high in oil (8-9% w/w)—all contents are presented on a dry basis.

In some embodiments, processing at least one of said lignocellulosic empty fruit bunches and lignocellulosic processing coproduct into a bioproduct uses known methods, including catalyzed processes and thermal processes. Catalyzed processes include according to various embodiments chemically catalyzed processes, biologically catalyzed processes and combinations thereof. Thus, according to an embodiment of the invention, such lignocellulosic material is treated for hydrolysis into fermentable compounds (e.g. carbohydrates) which are fermented to form the bioproduct. According to another embodiment, the lignocellulosic material is pyrolyzed to form a mixture of hydrocarbons and other organic compounds. According to still another embodiment, a thermal treatment converts lignocellulosic material into a syngas, which is further converted into said bioproduct.

Processing of fruit bunches according to commercial methods produce EFB, PPF, PKS, PKC and optionally other lignocellulosic materials. EFB, as formed in the process, has a high moisture content and is therefore unattractive as a means for energy generation. PPF has a lower moisture content and contains lipids, making its use more attractive. When commercial palm processing facilities produce both process steam and electricity, the total amount of PPF undergoes combustion. However, if only steam is to be produced, 70% of PPF remains unutilized and becomes a waste. PKS has a high energy value, but its use in burners or boilers designed for wood or fossil fuels necessitates a substantial modification of such equipment, which hinders its use for energy generation. The methods of the present invention, in marked contrast, provide for better utilization of these byproducts of palm oil production.

In some embodiments, the lignocellulosic material (EFB, PPF, PKS, PKC and any combination thereof) is thermally treated under conditions, which result in the generation of carbon compounds that are fermentable as such or after additional chemical processing, whose incorporation into the methods of this invention represents another embodiment of this invention.

According to one embodiment, conversion of lignocellulosic materials into fermentables comprises hydrolysis, wherein the polysaccharides are converted to monosaccharides (e.g. cellulose and hemi-cellulose are converted to dextrose and pentoses, respectively) or to oligomers of the same sugars. Lignin is not hydrolyzed and could be separated from the formed sugars and represents an energy source thereby generated.

In some embodiments, hydrolysis as described herein, comprises treatment with an acid, for example, but not limited to sulfuric acid or hydrochloric acid; treatment with an enzyme having cellulose hydrolyzing capability; treatment with an enzyme having hemi-cellulose hydrolyzing capability, or combinations thereof.

In some embodiments, hydrolysis of cellulose and of hemi-cellulose is preferably catalyzed. According to one embodiment, an acid is used as a catalyst, preferably a strong inorganic acid, such as sulfuric or hydrochloric acid. Acid catalyzed hydrolysis is conducted, according to different embodiments, at low, e.g. ambient temperature (e.g. when conducted with a concentrated acid solution) or at an elevated temperature (when a dilute solution of the acid is used). According to another embodiment, hydrolysis is enzymatically catalyzed, e.g. by enzymes having cellulose-hydrolyzing and/or hemicellulose hydrolyzing capacity. In another embodiment, the lignocellulosic material is pre-treated to facilitate enzymatic hydrolysis, e.g. by dilute acid treatment, thermal treatment, by ammonia or by a solvent that removes some of the lignin. According to a preferred embodiment, such enzymes are produced by fermentation of fermentables formed according to the method of the present invention and/or of a carbon compound in related aqueous effluents. According to a related embodiment, the lignocellulosic material is pre-treated to facilitate enzymatic hydrolysis, e.g. by dilute acid treatment, thermal treatment, by ammonia or by a solvent that removes some of the lignin. According to a preferred embodiment, such pre-treatment comprises contacting with the fermentation product for at least partial separation of lignin, thereby facilitating said hydrolysis.

According to an embodiment of the invention, lignocellulosic matter from processing FFB is used as a substrate for cultivation of mushrooms by solid-state fermentation.

In another embodiment, hydrolysis and fermentation are conducted simultaneously, such that accumulation of a high concentration of sugars and any potential inhibiting effects thereby are avoided (a practice referred to sometimes as simultaneous saccharification and fermentation, SSF, or simultaneous saccharification and co-fermentation, SSCF). In another preferred embodiment, an organism is used which has the capacity for both hydrolyzing and fermenting such sugars (a practice referred to sometimes as Consolidated bioprocessing (CBP). Organisms which may be utilized include *Saccharomyces cerevisiae*, and other yeasts, algae or bacteria as will be known to the skilled artisan.

In another embodiment of the methods of the present invention, the fermentables (monosaccharides, oligo-saccharides, and other organic compounds) are fermented to form a fermentation product. According to a preferred embodiment, in addition to fermentables produced by the conversion of lignocellulosic material, other carbon compounds, for example, solutes in POME are fermented, as well. In some embodiments, fermentation products suitable for use as fuels or fuel additives are of particular interest and are products of the methods of this invention. In some embodiments, such fermentation products useful as fuel or fuel additives may be produced by the methods described herein directly, or following chemical conversion of the fermentation product to yield the desired fuel or fuel additive. In a preferred embodiment, such fermentation products are selected from the group consisting of alcohols, hydrocarbons and esters.

In some embodiments, conversion of the sugars to fermentables comprises at least one of hydrolysis and thermal treatment.

In some embodiments, the fermentation product is an alcohol and in some embodiments, it is a low molecular weight alcohol, which in some embodiments is ethanol, or in some embodiments, the alcohol is selected from the group consisting of propanols, butanols and pentanols, such as, in some embodiments n-propanol, n-butanol and n-pentanol or isomers thereof or in some embodiments, the alcohol may comprise any combination of alcohols as herein described and as appropriate as will be known to one skilled in the art. According to alternative embodiments, essentially only one fermentation product is formed or fermentation produces multiple compounds, e.g. ethanol, butanol and acetone.

According to a preferred embodiment, the fermentation product is a low molecular weight alcohol with 2 to 5 carbon atoms, i.e. ethanol, n-propanol and its various isomers, n-butanol and its various isomers and n-pentanol and its various isomers.

In another embodiment, the fermentation product is an alcohol, which is formed in a fermentation liquor, and the methods of this invention further comprise the step of concentrating the alcohol by means of distilling the alcohol in a distillation column.

In some embodiments, fermentation is accomplished utilizing a suitable microorganism cultured in an aqueous medium containing the fermentable (obtained by processing the lignocellulosic material) and/or other carbon sources and optionally other nutrients, such as nitrogen compounds. According to a preferred embodiment, fermentation is conducted in specifically designed vessels (fermentors), or in some embodiments in non-specialized vessels, for example, fermentation may be conducted in POME-treatment ponds. Thus, in some embodiments, the fermentation products are formed in an aqueous medium, also referred to as fermentation liquor or fermentation broth. In preferred embodiments, the fermentation product is separated from the fermentation broth by known methods, such as solvent extraction, distillation, membrane separation, ion-exchange, chromatography, etc. According to a preferred embodiment, the fermentation product is $C_2$-$C_5$ alcohol, most preferably ethanol, and is separated from the fermentation liquor by means of distillation. In some embodiments, some of the fermentation products, e.g. many of the low molecular weight alcohols have an azeotrope, i.e. a composition where the compositions of the liquid phase and of the vapor phase are identical. Distillation in such cases forms an azeotropic solution. Concentration of that solution beyond azeotropic concentration may be achieved, in some embodiments, by adjusting the pressure in the distillation unit. In preferred embodiments, such concentration to beyond azeotropic concentration is accomplished by contacting the liquor with an adsorbent capable of selectively adsorbing water from the azeotropic solution. In some embodiments, ethanol recovery from ethanol-containing fermentation liquor, entails distillation, which forms a 95% ethanol azeotropic solution, which is then contacted with a molecular sieve to achieve more than 99% ethanol solutions.

According to another embodiment, multiple fermentation products are formed and at least one fermentation product is used, e.g. as an extractant, for the separation of the other. According to still another embodiment of the invention, another product of the method is used for such separation. Thus, according to a particular embodiment, palm oil triglycerides and/or fatty acids are converted into their ester form, e.g. methyl or ethyl esters, e.g. for use biodiesel, and such esters are used as solvents for the extraction of fermentation products from fermentation liquor. Extraction forms a solution of the fermentation product (e.g. an alcohol) in the triglyceride. According to one embodiment, such solution is further treated for the recovery of the fermentation product, e.g. by distillation. According to another embodiment, at least part of the fermentation product is left in the triglyceride and improves its performance as biodiesel, e.g. better performance at low temperatures. According to a preferred embodiment, multiple fermentation products are formed and separated from the fermentation broth and from each other. According to another embodiment, out of multiple fermentation products, some are left in the fermentation liquor. Thus, according to a preferred embodiment, fermentable compounds in an aqueous effluent, e.g. POME, are fermented to generate fermentation products that improve the nutrient and/or the fertilizer value of that effluent (e.g. single cell protein and organisms that produce nitrate) and/or lower the cost of POME treatment (e.g. enzymes, organisms or chemicals that facilitate clarification of POME.), which is a cost effective measure, resulting in reduction of costs associated with the separation of the fermentation products. According to an embodiment of the method, the fermentation product is volatile and separated from the fermentation liquor by distillation, the non-volatile content of the liquor is left in the bottom of the distillation unit and at least part of that non-volatile content is combined with treated (e.g. fermented) POME to generate a feed ingredient with high nutritional value.

According to another preferred embodiment, the fermentation product is a monomer for the polymer industry, e.g. for the production of poly-hydroxy-alkanoate.

According to another preferred embodiment, the fermentation product is at least one enzyme, most preferably an enzyme that is used in the processing of the palm fruit, the production of the fermentation product, the treatment of the effluent, the production of the third product and various combinations of those. According to various examples, produced enzymes are used for clarification, for catalyzing esterification or trans-esterification, for the hydrolysis of lignocellulosic matter, etc.

According to still another embodiment, the fermentation product is high value compound selected from anti-oxidant, carotenoids and other nutraceuticals. Typically, those are formed at low concentration and/or intracellularly. High energy availability and separation by means of contact with another fermentation product, according to the method of the present invention, lowers the production cost. Production of such high value compounds is particularly attractive for production in remote locations, such as next to palm oil mills.

According to an embodiment of the invention, the fermentation product is extracted by another fermentation product of the method or by another product of the method (e.g. fatty acid esters) and fermentation is operated in a continuous mode. According to this embodiment, extraction is used to maintain low concentration of fermentation product in the fermentation liquor, thereby avoiding product inhibition of the fermentation and increasing thereby fermentation productivity.

In some embodiments, processing the fruit comprises extraction of an oil derived from at least one of the digested fruit, press cake, separated fine solids, aqueous effluents and products of treatment of such effluents, kernel cake or combinations thereof.

In some embodiments, oil extraction is by means of said fermentation product, products thereof and combinations thereof.

In some embodiments, oil extraction is by means of concentrated solutions of a fermentation product selected from the group of alcohols, whereby an extract is formed comprising said oil and said alcohol.

In some embodiments, the oil is recovered from the extract by adding water to said extract, whereby an oil phase and a diluted alcohol phase are formed.

The term oil refers herein to triglycerides of fatty acids or a composition rich in such triglycerides, e.g. containing at least 98% of triglycerides (at least 90% in case of crude oil).

According to a preferred embodiment, at least part of the oil present originally in the fruit is recovered by solvent extraction, rather than or in addition to the above-described method (i.e. mashing, screw pressing the pulp to separate the crude oil, clarification in decanters, kernel separation, milling the nuts, etc.). In some embodiments, during solvent extraction, an oil bearing fraction of the fruit and/or a product of its processing is contacted with an organic solvent in which the oil dissolves to form a solution of oil in the solvent, also referred to as miscella. Subsequent to formation of the solution, the oil is separated from the solvent in the miscella. Solvent-extraction based recovery of oil is well known in the art and practiced in many oilseed processing industries. In preferred embodiments, the extractant used is hexane or a mixture of hexane isomers and oil/solvent separation from the miscella is conducted by distillation of the hexane.

According to a preferred embodiment of the present invention, an oil bearing fraction of the fruit and/or a product of its processing is contacted with an organic solvent. In some embodiments, an organic solvent is contacted with at least one of the digested fruit, palm press pulp fiber (containing about 8-9% oil), separated fine solids, POME or products of its processing, kernels, milled kernels and oil-wetted adsorbents (used for bleaching) and filter aids. In some embodiments, free fatty acids (FFAs) present are also extracted by oil extracting solvents. In some embodiments, the pH is lowered to be below 7 by the addition of an acid, for example, so that salts of the fatty acids which are poorly extracted at higher pH may be extracted more efficiently.

In some embodiments, the solvent is contacted with a component containing FFAs, and no oil. According to this aspect and in one embodiment, only FFAs are extracted. Thus, upon contact with the solvent, oil, FFAs or both are extracted to the solvent and form a miscella containing the solvent and the extracted component.

According to a preferred embodiment, the solvent used in the extraction of oil, FFAs or both is selected from a group consisting of fermentation product produced according to the method of the present invention, e.g. alcohols; hydrocarbons and esters, products of their chemical conversion and their combinations. Hydrocarbons (directly formed in fermentation or from fermentation products) and fatty acid esters are good extractants for oil and FFAs. Heavier alcohols and lighter alcohols, when in concentrated solutions act as extractants for such purposes, as well.

According to a preferred embodiment, oil, FFAs or both are extracted with concentrated alcohol solutions, e.g. ethanol-water solution where ethanol concentration is greater than 90%, as formed in the ethanol distillation column. A miscella comprising ethanol, oil and/or FFAs is formed. According to a related preferred embodiment, oil and/or FFAs may be separated from the solvent in the miscella to form separated oil and/or FFAs and separated solvent. According to a preferred embodiment the extracting solvent is a concentrated solution of ethanol and separation of the oil/FFAs is conducted by the addition of water to the miscella. Such addition generates separated oil/FFAs and an aqueous solution of ethanol, e.g. of ethanol concentration of about 50%. Such aqueous solution of ethanol is re-concentrated, according to a preferred embodiment by distillation, preferably using the distillation column where ethanol is separated from the fermentation liquor.

In other embodiments, the miscella is used without separating the oil/FFAs as an oil/FFAs source for the production of fatty acid esters, e.g. ethyl esters of fatty acids. Addition of a suitable catalyst to the miscella as such, or after some modification thereof (e.g. removal of co-extracted water) forms said ethyl ester and glycerol. Chemical or biological catalysts may be used in this context. In some embodiments, the reaction of oil with ethanol (trans-esterification) utilizes basic catalysts as preferred chemical catalysts, while for the reaction of FFAs with ethanol (esterification), acidic catalysts are preferred.

According to a related embodiment, the fermentation product is an alcohol and FFAs from said processing of fruits are converted to fatty acid esters by an esterification reaction with said alcohol. According to said embodiment, a stream comprising said FFAs is reacted with a stream comprising said alcohol. According to various embodiments, streams comprising FFAs are selected from FFAs removed from crude oil by distillation, soapstock acidulated with an acid (e.g. sulfuric acid), FFAs separated from POME and low grade oil rich in FFAs. According to various embodiments, alcohol-comprising streams are selected from streams formed in the separation of said alcohol, e.g. by distillation.

Replacing at least part of commercial palm oil extraction with a solvent-extraction based process decreases the amount of generated waste stream (effluents), e.g. POME. Such replacement results in major saving in costs related to treating these effluents and in the reduction of related methane and $CO_2$ emissions, which also has high carbon credit commercial value.

According to another embodiment, contacting with a solvent for oil extraction obviates the need for sterilization and thereby reduces the costs related to such operation, including reducing the amount of formed high-BOD aqueous effluent.

In another embodiment, the extract is used for the production of a fatty acid ester. In another embodiment, the fermentation product is an alcohol, and the method further comprises the step of reacting palm oil with said alcohol and producing a fatty acid ester of said alcohol.

In another embodiment, the fermentation product is ethanol and a fatty acid ester is formed, wherein the method further comprises the step of mixing ethanol with said ester for the formation of biodiesel.

According to a preferred embodiment, a fatty acid ester is formed by at least one of trans-esterification of palm oil triglycerides with an alcohol and esterifying palm oil free fatty acids (FFAs) with an alcohol and said ester is mixed with a fermentation product to form biodiesel. Production of esters from oil for use in biodiesel (typically methyl esters, but ethyl and other esters could also be used) is well known and practiced on large industrial scale. Esters formed from palm oil (and related FFAs) are less suitable for use at low temperature conditions due to relatively high crystallization point, also referred to as unfavorable cold flow. Studies have found that mixing such esters with low molecular weight alcohols, e.g. ethanol provides at least partial solution to that problem. E.g. ethanol blending lowers the cloud point of the blended fuel and significantly reduces smoke emissions from the engine without deteriorating other emissions and thermal efficiency. The reduced smoke emissions enable the engine to retard fuel injection timing to reduce NOx emissions.

Alternatively, the improved fuel (esters blends with fermentation product) is formed on using such esters for the extraction of fermentation products from fermentation liquor. Studies have shown that a fuel formed on extracting the fermentation products from an ABE (acetone, butanol and ethanol) fermentation with esters of palm fatty acids has properties comparable to that of No. 2 diesel, but their cetane numbers and the boiling points of the 90% fractions were higher. Therefore, they could serve as efficient No. 2 diesel substitutes.

According to still another embodiment, the cold flow performance of palm fatty acid esters are improved by forming butyl esters of those fatty acid through the reaction of palm oil triglycerides and/or fatty acids with butanol fermentation product. The pour point of the product is 5.0° C., markedly lower than that of palm oil methyl ester, 12.5 C. The product has good ignitability.

In another embodiment, the at least one fatty compound is extracted by means of said fermentation product, wherein said fatty compound is selected from a group consisting of fatty acids, oils and low-grade oil, and the method further comprises the step of reacting said fatty compound with an alcohol to form their ester.

The term fatty compounds refers to an oil, a free fatty acid or acids and any combination thereof.

In another embodiment, the fermentation product is an alcohol and the fatty acids are reacted with the alcohol. In some embodiments, the fatty acids are reacted with a fermentation product.

According to another preferred embodiment, the third product is a biological compound other than the fermentation products described hereinabove. According to various embodiments, biological compounds comprise a non-oil, non-alcohol, non-ester product or co-product of the processing of the fruit or EFB. In some embodiments, such third product comprises a compound present in the crude oil and in streams formed upon its refining (e.g. in the gums and soapstock), in PPF, in PKS, in PKC, in condensed distillates of deodorizing, in the aqueous streams formed in the separation and processing steps of the methods of this invention, and in combinations thereof.

According to another embodiment, the biological compound is selected from the group consisting of vitamins, including Vitamin A and Vitamin E, flavonoids, lycopene, phenolic acids, hydroxy acids, sugars, fertilizers, single-cell protein monomers for the polymer industry, polymerizable compounds, acetone, enzymes, tocotrienols and carotenoids. Polymerizable compounds include, among others, hydroxylcarboxylic acids, e.g. lactic acid and hydroxy-butyric acid and amino acids, such as aspartic and glutamic acids.

According to a preferred embodiment, the biological compound is separated by means of a fermentation product formed in the methods of this invention. The term separated refers to at least one of the methods of concentration (i.e. increasing its concentration in a medium, such as an aqueous solution) and/or purification (i.e. increasing the ratio between that compound and impurities). According to a preferred embodiment, separation is conducted by means of solvent extraction, where the fermentation product is the extractant for the biological compound or for an impurity.

According to an embodiment of the invention, the biological compound is separated from the aqueous effluents of FFB processing, e.g. POME, which typically contains vitamins (C, the B-complex vitamins, folic acid), flavonoids, phenolic acids, hydroxy acids, sugars and minerals. According to various embodiments, the compound is separated from POME as such, from pre-treated POME or from a combination of those.

Hence, according to a preferred embodiment, POME is pretreated prior to the separation of the biological compound in at least one operation selected from a group consisting of separation of fatty materials (mainly triglycerides and FFAs), clarification and concentration by water removal (e.g. via distillation or membrane separation). Thus, according to a related preferred embodiment, POME is clarified, treated for water separation (which water is reused in the process) and the reside is treated for separation of the biological product, preferably by extraction. According to a preferred embodiment, the residue after the separation of the biological product is used as at least one of a fertilizer, a feed ingredient or a substrate for fermentation.

According to other embodiments, the biological compound is a product of converting at least one compound present originally in the fruit, e.g. by chemical of biological conversion. Preferably, said conversion is biological and is catalyzed or conducted by enzymes and/or living microorganism, e.g. bacteria, yeast or algae. According to particularly preferred embodiments, the biological compound is produced by at least one of algae grown in said aqueous stream (e.g. POME), by fermenting carbon sources in such aqueous stream and by fermenting said fermentables. According to a preferred embodiment, the producing algae or a fermenting cell is cultivated in such aqueous stream as such or after some modification, optionally in POME treating ponds.

In some embodiments, the third product is a biological compound and said biological compound is separated by means of said fermentation product formed as herein described.

According to an embodiment of the invention, the biological compound is formed by a conversion of lignocellulosic matter (EFB, PPF, PKC, PKS), which conversion is selected from chemically catalyzed reactions, biologically catalyzed reactions, thermal treatments and their combinations. According to a particularly preferred embodiment, the biological product is a biofuel. According to a preferred embodiment, bio-oil is formed through pyrolysis, which bio-oil comprises at least one of acids, alcohols, aldehydes, ketones, esters, heterocyclic derivatives and phenolic compounds. According to other preferred embodiments, the biological compound is selected from a group consisting of hydrogen, synthesis gas and products of their conversion, including liquid hydrocarbon fuels, such as gasoline, naphta and diesel, alcohols such as methanol, ethanol and others, and combinations thereof. According to another preferred embodiment, the biological compound, e.g. selected from the above-listed ones, provides fermentable material for the production of other biological products.

According to still another preferred embodiment, the biological product is formed by chemical, biological or thermal conversion (e.g. cracking) of the palm oil, of crude palm oil, of FFAs, of other streams containing organic compounds and their combinations.

According to other embodiments, that biological compound is selected from a group consisting of product and co-products of processing said fruit or EFB, e.g. a compounds present in the crude oil and in streams formed on its refining (e.g. in the gums and soapstock), in PPF, in PKS, in PKC, in condensed distillates of deodorizing, in the aqueous stream formed in providing, in the aqueous stream formed in processing, and in combinations of those. According to another embodiment, the biological compound is selected from a group consisting of vitamins, flavonoids, phenolic acids, hydroxy acids, sugars, fertilizers, single-cell protein, monomers for polymer industry, acetone, enzymes, and carotenoids.

According to a preferred embodiment, the biological compound is separated by means of a fermentation product formed in step (f). As used here, separated means at least one of concentration (i.e. increasing its concentration in a medium, such as an aqueous solution) and purification (i.e. increasing the ratio between that compound and impurities). According to a preferred embodiment, said separation is conducted by means of solvent extraction, where the fermentation product is the extractant for the biological compound or for an impurity.

According to various embodiments, POME contains flavonoids and the fermentation products or the products of their conversion are water-insoluble esters of carboxylic acids or of fatty acids. Thus, according to one embodiment, the fermentation product is a carboxylic acid, such as acetic, lactic or citric. Such acid is reacted with an alcohol, optionally also formed by fermentation from fermentable material, to form the ester of the acid and the alcohol. According to another embodiment, the ester is a fermentation product, e.g. an ester of a fatty acid. According to still another embodiment, the fermentation product is an alcohol, such as ethanol, a propanol or a butanol, and is reacted with palm oil or palm fatty acid to form the palm oil ester of the alcohol. According to a related embodiment, POME is first clarified and concentrated and then contacted with the water-insoluble ester, whereby the flavonoids transfer into the organic phase. According to a related embodiment, the flavonids are recovered from the organic phase by contacting with an alkaline aqueous solution.

In some embodiments, the third product is formed by biological conversion.

In some embodiments, the biological conversion is selected from a group consisting of (i) growing algae in said generated aqueous stream, (ii) fermenting carbon sources in said aqueous stream and (iii) fermenting said fermentables and combinations thereof.

In some embodiments, a wet matter is formed and the fermentation product, preferably ethanol, is contacted with the wet matter to form dried matter and diluted ethanol. Such wet matter, according to various embodiments, is selected from a group consisting of POME-treating sludge, said fine solids, PPF, PKS, PKC, byproducts of hydrolyzing lignocellulosic material, cell mass and combinations thereof. Oil that gets to the anaerobic pond tends to agglomerate with the rising solids brought up by the biogas and form a sticky scum that is difficult to remove. Solids tend to build up in the ponds. Regular de-sludging of the ponds is required. According to a preferred embodiment, such solids form the wet matter to be dried.

According to a preferred embodiment, the fermentation product is liquid at ambient temperature and pressure and of high miscibility with water, e.g. ethanol, propanol, acetone, and tert-butanol. According to a particularly preferred embodiment, said fermentation product is ethanol. Contacting such wet matter, particularly if said matter in dry form is of low solubility in the fermentation product, with the fermentation product results in the formation of dried matter and a liquid comprising the fermentation product and increased concentration of water compared with the water content of the fermentation product prior to said contacting. The dried matter is separated from the liquid. According to a preferred embodiment, the liquid is treated for further use. Such further use includes recycle to such drying operation. According to various embodiments, treating comprises at least one of water removal and purification. According to a preferred embodiment, said fermentation product is ethanol and said treating is conducted in a distillation unit wherein ethanol is recovered from fermentation liquor.

In some embodiments, the fermentation product is ethanol and a fatty acid ester is formed in the methods of this invention, preferably palm oil fatty acid ester, where the method further comprises the step of mixing the ethanol with the ester to form a biodiesel. In some embodiments, the methods of this invention comprise mixing a fermentation product other than ethanol with the ester to form a biodiesel.

In some embodiments, the method further comprises the step of treating said at least one of said gums, fatty acids and fatty acid alkali salt with said fermentation product.

In some embodiments, the method further comprises the step of fractionating said oil by means of extraction with said fermentation product.

In some embodiments, the third product is selected from a group consisting of vitamins, flavonoids, phenolic acids, hydroxy acids, sugars, fertilizers, single-cell protein monomers for the polymer industry, polymerizable compounds, acetone, enzymes, and carotenoids.

In some embodiments, the ester is selected from the group consisting of esters of fatty acids.

According to a preferred embodiment, the esters are of fatty acids, e.g. methyl, ethyl, propyl or butyl esters of fatty acids.

In some embodiments, producing said third product comprises extraction from at least one of aqueous stream generated in said providing step, aqueous stream generated in said processing step and combinations thereof.

In some embodiments, extraction is by means of said fermentation product, products thereof and their combinations.

In some embodiments, the method further comprises step of pre-treating said aqueous stream prior to said extraction, wherein said pre-treating comprises at least one of concentration and separation of insolubles.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An integrated method for the processing of palm fruit bunches to oil and other products, said method comprising:
   a. providing palm fruit carrying bunches and separating said palm fruit carrying bunches into fruits and lignocellulosic empty fruit bunches;
   b. processing said fruits to form palm oil, and at least one lignocellulosic processing coproduct;
   c. generating an aqueous stream while carrying out step (a), step (b) or both;
   d. producing a non-oil, non-alcohol, non-fatty acid ester third product from said oil, said lignocellulosic processing coproduct, said aqueous stream or from a combination thereof;
   e. processing at least a portion of said lignocellulosic empty fruit bunches, lignocellulosic processing coproduct or a combination thereof into a fourth product and optionally producing at least one fifth conversion product from said fourth product; and f. using at least a portion of said fourth product or a product of its conversion or a combination thereof in said processing in step (b) said producing in step (d), or in a combination thereof.

2. The method of claim 1, wherein said fourth product is a fermentable compound, and said method comprises fermenting said fermentable compound into a fermentation product said fermentation product being the fifth product.

3. The method according to claim 2, wherein said fermentation product is selected from the group consisting of alcohols; hydrocarbons and esters.

4. The method according to claim 3, wherein said fermentation product is an ester and said ester is selected from the group consisting of esters of fatty acids.

5. The method according to claim 2, wherein said fermentation product is an alcohol formed in a fermentation liquor, and said method further comprises the step of concentrating said alcohol in a distillation column.

6. The method according to claim 2, wherein said fermentation product is an alcohol, and said method further comprises the step of reacting said palm oil, palm oil fatty acids or both with said alcohol and producing a fatty acid ester of said alcohol.

7. The method according to claim 2, wherein said fermentation product is an alcohol selected from the group consisting of ethanol, propanols, butanols and pentanols or a combination thereof.

8. The method according to claim 2, wherein a fatty acid is reacted with said fermentation product.

9. The method according to claim 2, wherein at least one fatty compound is extracted by means of said fermentation product, wherein said fatty compound is selected from a group consisting of fatty acids, oil and low-grade oil, further comprising the step of reacting said fatty compound with an alcohol to form their ester.

10. The method according to claim 9, wherein said fermentation product is an alcohol and wherein said fatty compound is reacted with said alcohol.

11. The method according to claim 2, wherein said processing of at least a portion of said lignocellulosic empty fruit bunches, lignocellulosic processing coproduct or a combination thereof comprises hydrolysis, thermal treatment or a combination thereof.

12. The method according to claim 11, wherein said hydrolysis comprises treatment with sulfuric acid, hydrochloric acid, another acid, enzymes with cellulose hydrolyzing capacity, enzymes with hemi-cellulose hydrolyzing capacity, and combinations thereof.

13. The method according to claim 2, wherein a wet matter is formed and wherein said fermentation product is ethanol, and said method further comprises a step of drying said wet matter by contacting said wet matter with ethanol to form dried matter and diluted ethanol.

14. The method according to claim 2, further comprising the steps of producing a biodiesel by producing a palm-oil ester and mixing the fermentation product with said ester.

15. The method of claim 1, wherein at least one of said third product, said fourth product and said fifth product is selected from a group consisting of a vitamin, a flavonoid, a phenolic acid, a hydroxy acid, a sugar, a fertilizer, a polymerizable compound, acetone, an enzyme, a carotenoid and combinations thereof.

16. The method according to claim 1, wherein said method further comprises treating said palm fruit carrying bunches with steam, water or a combination thereof at elevated temperatures and generating said aqueous stream.

17. The method according to claim 1, wherein processing said fruits comprises digestion, pressing to form crude oil and press cake, separation of fine solids from the crude oil, clarification of said crude oil forming clarified oil and an aqueous effluent, dehydration of clarified oil to form dehydrated clarified oil, treating said press cake for separation of nuts from palm press fiber, cracking said nuts to separate kernels from the palm kernel shell, milling said kernels for extracting palm kernel oil and separating said palm kernel oil from palm kernel cake or combinations thereof.

18. The method according to claim 17, wherein said processing further comprises refining said clarified oil, dehydrated clarified oil, palm kernel oil or combinations thereof and wherein refining comprises de-gumming, de-acidification or combinations thereof, and producing a refined oil and at least one of a gum, a fatty acids and a fatty acid alkali salt.

19. The method of claim 18, wherein said fourth product is a fermentable compound, and said method comprises fermenting said fermentable compound into a fermentation product.

20. The method according to claim 19, further comprising the step of treating at least one of said gum, fatty acid and fatty acid alkali salt with said fermentation product.

21. The method according to claim 19, further comprising the step of fractionating said oil by means of extraction with said fermentation product.

22. The method according to claim 18, wherein said processing generates an aqueous stream, which comprises an aqueous effluent.

23. The method according to claim 17, wherein said lignocellulosic processing coproduct comprises a palm press fiber, a palm kernel shell, a palm kernel cake or combinations thereof.

24. The method according to claim 17, wherein processing said fruit comprises oil extraction from digested fruit, press cake, separated fine solids, aqueous effluent or products of its treatment, kernel cake or combinations thereof.

25. The method of claim 24, wherein said method comprises processing said lignocellulosic empty fruit bunches, lignocellulosic processing coproduct or a combination thereof into a fermentable product and said method comprises fermenting said fermentable product into a fermentation product.

26. The method according to claim 25, wherein said oil extraction is by means of said fermentation product, products thereof and their combinations.

27. The method according to claim 25, wherein said oil extraction utilizes a concentrated solution of a fermentation product selected from the group of alcohols, and said method further comprises the step of forming an extract comprising said oil and said alcohol.

28. The method according to claim 27, wherein said oil is recovered from said extract by adding water to said extract, whereby an oil phase and a diluted alcohol phase are formed.

29. The method according to claim 27, wherein said extract is used for the production of a fatty acid ester.

30. The method according to claim 1, wherein said fourth or fifth product is an ester.

31. The method according to claim 30, wherein said ester is an ester of a fatty acid.

32. The method according to claim 1, wherein producing at least one of said third product, said fourth product and said fifth product comprises extraction of said third or fourth product from said aqueous stream or from aqueous fermentation liquor.

33. The method of claim 32, wherein said third product is a fermentable product and said method comprises fermenting said fermentable product into a fermentation product.

34. A method according to claim 32, wherein said extraction is by means of said fermentation product, products thereof and their combinations.

35. The method according to claim 34, further comprising the step of concentrating said aqueous solution, separating insoluble materials in said aqueous stream or both prior to extraction.

36. The method according to claim 1, wherein said third product is a biological compound.

37. The method according to claim 36, wherein said biological compound is formed by biological conversion.

38. The method of claim 36, wherein at least one of said third product, fourth product and fifth product is a fermentation product and wherein said biological compound is separated utilizing said fermentation product.

39. The method of claim 38, wherein said fourth product is a fermentable compound, and said method comprises fermenting said fermentable compound into a fermentation product.

40. The method according to claim 38, wherein said biological conversion is selected from a group consisting of (i) growing algae in said generated aqueous stream, (ii) fermenting carbon sources in said aqueous stream and (iii) fermenting said fermentable compounds and combinations thereof.

* * * * *